US005500409A

United States Patent [19]
Tan et al.

[11] Patent Number: 5,500,409
[45] Date of Patent: Mar. 19, 1996

[54] METHOD FOR INHIBITING COLLAGEN SYNTHESIS BY KELOID FIBROBLASTS

[75] Inventors: Elaine M. L. Tan; Jouni J. Uitto, both of Gladwyne, Pa.

[73] Assignee: Thomas Jefferson University, Philadelphia, Pa.

[21] Appl. No.: 32,714

[22] Filed: Mar. 17, 1993

Related U.S. Application Data

[63] Continuation of Ser. No. 591,407, Oct. 1, 1990, abandoned.
[51] Int. Cl.$^6$ ................................................ A61K 38/18
[52] U.S. Cl. .......................... 514/2; 514/56; 514/838; 530/399
[58] Field of Search ........................ 514/56, 2, 838, 514/54, 21; 424/423, 424, 425, 426, 422, 443–445, 446; 530/356, 399; 536/23.1

[56] References Cited

U.S. PATENT DOCUMENTS

| | | | |
|---|---|---|---|
| 4,745,098 | 5/1988 | Michaeli | 514/2 |
| 4,760,131 | 6/1988 | Sundsmo et al. | 530/356 |
| 4,808,570 | 2/1989 | Michaeli | 514/2 |
| 4,837,024 | 6/1989 | Michaeli | 424/446 |
| 4,879,282 | 11/1989 | Saliba, Jr. | 514/56 |
| 4,883,755 | 11/1989 | Carabasi et al. | 514/2 |
| 4,889,808 | 12/1989 | Rappaport | 514/8 |
| 4,950,483 | 8/1990 | Ksander et al. | 424/422 |
| 5,026,839 | 6/1991 | Moscatelli et al. | 536/23.1 |
| 5,120,715 | 6/1992 | Kato et al. | 514/21 |
| 5,155,214 | 10/1992 | Baird et al. | 530/399 |
| 5,189,148 | 2/1993 | Akiyama et al. | 530/399 |

OTHER PUBLICATIONS

Sigma Chemical Company Catalog, p. 444 (1990).
Burgess et al., "Structural evidence that endothelial cell growth factor β . . . ", PNAS 83:7216–7220 (Oct. 1986).
Turck et al. (1989), Immunology, vol. 68: pp. 410–415.
Finesmith et al. (1990) Journal of Cellular Physiology. vol. 144: pp. 99–107.
Odedra et al. (1987) Biochemical and Biophysical Research Communications vol. 143, No. 3, pp. 947–953.
Broadley et al. (1988) Int. J. Tiss. Reac. vol. 6: pp. 345–353.
Buckley–Sturrock et al. (1989) Journal of Cellular Physiology, vol. 138: pp. 70–78.
Kelly, A. P. Keloids, Dermatol. Clin. 6:413–424, (1988).
Berman, B., and M. R. Duncan, "Short–term keloid treatment in vivo with human interferon alfa–2b results in a selective and persistent normalization of keloidal fibroblast collagen, glycosaminoglycan, and collagenase production in vitro", J. Am. Acad. Dermatol. 21:694–702 (1989).
Panabiere–Castaings, M. H., "Retinoic acid in the treatment of keloids", J. Dermatol. Surg. Oncol., 14: 1275–1276 (1988).
Daly, T. J., and W. L. Weston, "Retinoid effects on fibroblast fibrotic disease in vivo", J. Am. Acad. Dermatol., 15:900–902 (1986).
Clowes A. W., and M. J. Karnovsky, "Suppression by heparin of smooth muscle cell proliferation in injured arteries", Nature 265:625–626 (1977).
Castellot, J. J. Jr., A. M. Kambe, D. E. Dobson, and B. M. Spiegelman, "Herparin potentiation of 3T3–adipocyte stimulated angiogenesis: mechanisms of action of endothelial cells", J. Cell Physiol., 127:323–329 (1986).
Ehrlich, H. P., W. K. Jung, D. E. Costa, and J. B. M. Rajaratnam, "Effects of heparin on vascularization of artificial skin grafts in rats", Exp. Molec. Pathol., 48:244–251 (1988).
Joseph–Silverstein, J. and D. B. Rifkin, "Endothelial cell growth factors", Semin. Thromb. Hemost., 13:504–513 (1987).
Brown, C. C. and G. Balian, "Effect of heparin on synthesis of short chain collagen by chondrocytes and smooth muscle cells" J. Cell Biol., 99:1688–1695 (1987).
Graham, M. T., D. E. Drucker, H. A. Perr, R. F. Diegelmann, H. P. Ehrlich, "Heparin modulates human intestinal smooth muscle cell proliferation, protein synthesis and lattice contraction", Gastroenterology 93:801–809 (1987).
Lyons–Giordano, B., H. Conaway, and N. A. Kefalides, "The effect of heparin on fibronectin and thrombospondin synthesis by human smooth muscle cells", Biochem. Biophys. Res. Commun., 148:1264–1269 (1987).
Damon, D. H. et al. "Heparin potentiates the action of acidic fibroblast growth factor by prolonging its biological half–life", J. Cell. Physiol.).
Thornton, S. C., S. N. Mueller, and E. M. Levine, "Human endothelial cells: use of heparin in cloning and long–term serial cultivation", Science, 222:623–625 (1983).
Maciag, T., T. Mehlman, and R. Friesel, "Heparin binds endothelial cell growth factor, the principal endothelial cell mitogen in bovine brain", Science, 225:932–935 (1984).
Gospodarowicz, D. and J. Cheng, "Heparin protects basic and acidic fibroblast growth factor from inactivation", J. Cell. Physiol., 475–484 (1986).
Shreiber, A. B. et al. "The interaction of endothelial cell growth factor with heparin", Proc. Natl. Acad. Sci. USA, 82:6138–6142, (1985).
Tan, E. M. L. et al. "Heparin and endothelial cell growth factor modulate collagen proteoglycan production in human smooth muscle cells", Biochem. Biophys. Res. Commun., 163:84–92 (1989).
Juva, K. and D. J. Prockop, "Modified procedure for the assay of $H^3$– or $C^{14}$–labeled hydroxyproline", Anal. Biochem. 15:77–83 (1966).
Bradford, M. M., "A rapid and sensitive method for the quantitation of microgram quantities of protein utilizing the principle of protein–dye binding" Anal. Biochem., (List continued on next page.)

Primary Examiner—Stephen G. Walsh
Attorney, Agent, or Firm—Jane Massey Licata

[57] ABSTRACT

A composition for the treatment of skin fibrotic and other cirrhotic diseases comprising an endothelial cell growth factor, either alone or in combination with heparin or a heparin-like compound is provided. Methods for the treatment of skin fibrotic and other cirrhotic diseases and for inhibition of collagen synthesis by skin fibroblasts using an endothelial cell growth factor either alone or in combination with heparin or a heparin-like compound are also provided.

6 Claims, 8 Drawing Sheets

OTHER PUBLICATIONS

72:248–254 (1976).

Burton, K., "Determination of DNA concentration with diphenylamine", *Methods Enzymol.* 12B:163–166 (1968).

Oikarinen, H., A. 1. Oikarinen, E. M. L. Tan, R. P. Abergel, "Modulation of procollagen gene expression by retinoids", *J. Clin. Invest.*, 75:1545–1553 (1985).

Maniatis, T., A. Jeffrey, and D. G. Kleid, "Nucleotide sequence of the rightward operator of phage" *Proc. Natl. Acad. Sci. USA*, 72:1184–1188 (1975).

Uitto, J. et al. "Altered steady–state ratio of type I/type III procollagen mRNAs correlates with selectively increased type I procollagen biosynthesis in cultured keloid fibroblasts", *Proc. Natl. Acad. Sci. USA*, 82:5935–5939 (1985).

Thomas, P. S., "Hybridization of denatured RNA and small DNA fragments transferred to nitrocellulose", *Proc. Natl. Acad. Sci. USA*, 77:5201–5205 (1980).

Chu, M. L., J. C. Myers, M. P. Bernard, D. F. Ding, and F. Ramirez, "Cloning and characterization of the five overlapping cDNAs specific for the human pro–alpha 1(I) collagen", *Nucleic Acids Res.*, 10:5925–5934 (1982).

Bernard, M. P., M. Kolbe, D. Weil, and M. L. Chu, "Human cellular fibronectin: comparison of the carboxyl–terminal portion with rat identified primary structural domain separated by hypervariable regions" *Biochemistry*, 24:2698–2704 (1985).

Ponte, P. et al. "Human actin genes are single copy for alpha–skeletal and alpha–cardiac actin but multicopy for beta– ad gamma–cytoskeletal genes: 3' untranslated regions are isotype specific but are conserved in evolution", *Mol. Cell. Biol.*, 3:1783–1791 (1983).

METHOD FOR INHIBITING COLLAGEN SYNTHESIS BY KELOID FIBROBLASTS

This is a continuation of application Ser. No. 07/591,407, filed Oct. 1, 1990, now abandoned.

BACKGROUND OF THE INVENTION

Skin fibrotic and cirrhotic diseases are characterized by excessive collagen synthesis. For example, keloids are cutaneous lesions composed of excess accumulation of extracellular matrix. The predominant matrix component that is increased is collagen. Several treatment modalities are available including intralesional injections of glucocorticosteroids, surgical excision, cryotherapy and compression (Kelly, A. P. Keloids, *Dermatol. Clin.* 6:413–424, (1988)). Intralesional injections of human interferon alpha-2b (Berman, B., and M. R. Duncan, "Short-term keloid treatment in vivo with human interferon alfa-2b results in a selective and persistent normalization of keloidal fibroblast collagen, glycosaminoglycan, and collagenase production in vitro" *J. Am. Acad. Dermatol.* 21:694–702 (1989)); and topical applications of retinoids, (Panabiere-Castaings, M. H., "Retinoic acid in the treatment of keloids" *J Dermatol Surg. Oncol.*, 14:1275–1276 (1988); Daly, T. J., and W. L. Weston, "Retinoid effects on fibroblast proliferation and collagen synthesis in vitro and on fibrotic disease in vivo", *J Am Acad Dermatol.*, 15:900–902 (1986)), have also been employed. In the majority of therapeutic modalities, variable success has been encountered. Therefore, other alternative therapies need to be developed.

Heparin and endothelial cell growth factor are capable of influencing a variety of biologic activities of many cell types (for example, Clowes A. W., and M. J. Karnovsky, "Suppression by heparin of smooth muscle cell proliferation in injured arteries", *Nature* 265:625–626 (1977); Casteliot, J. J. Jr., A. M. Kambe, D. E. Dobson, and B. M. Spiegelman, "Heparin potentiation of 3T3-adipocyte stimulated angiogenesis: mechanisms of action of endothelial cells", *J Cell Physiol.*, 127:323–329 (1986); Ehrlich, H. P., W. K. Jung, D. E. Costa, and J. B. M. Rajaratnam, "Effects of heparin on vascularization of artificial skin grafts in rats", *Exp. Molec Pathol.*, 48:244–251 (1988); Joseph-Silverstein, J. and D. B. Rifkin, "Endothelial cell growth factors", *Semin Thromb. Hemost.*, 13:504–513 (1987)).

Heparin, a highly negatively-charged glycosaminoglycan, has been demonstrated to inhibit vascular smooth muscle cell proliferation both in vivo and in vitro (A. W. Clowes et al., supra). Heparin has also been found to promote angiogenesis (J. J. Casteliot, Jr. et al., supra); modulate the synthesis of collagen by chondrocytes (Brown, C. C. and G. Balian, "Effect of heparin on synthesis of short chain collagen by chondrocytes and smooth muscle cells", *J. Cell Biol.*, 99:1688–1695 (1987)); and intestinal smooth muscle cells (Graham, M. T., D. E. Drucker, H. A. Perr, R. F. Diegelmann, H. P. Ehrlich, "Heparin modulates human intestinal smooth muscle cell proliferation, protein synthesis and lattice contraction", *Gastroenterology* 93:801–809 (1987)); and stimulate the synthesis of fibronectin and thrombospondin by human smooth muscle cells (Lyons-Giordano, B., H. Conaway, and N. A. Kefalides, "The effect of heparin on fibronectin and thrombospondin synthesis by human smooth muscle cells", *Biochem. Biophys. Res. Commun.*, 148:1264–1269 (1987)).

Endothelial mitogens, such as endothelial cell growth factor (ECGF), are expressed by various cells and tissues. ECGF exhibits various biologic effects in cell culture and is mitogenic for a variety of cell types, that include endothelial cells (J. Joseph-Silverstein et al., supra). Furthermore, ECGF has a strong affinity for heparin (J. Joseph-Silverstein et al., Supra). Heparin prolongs the half-life of the growth factor and is, therefore, able to potentiate the biologic activities of ECGF (Damon, D. H., R. R. Lobb, P. A. D'Amore, and J. A. Wagner, "Heparin potentiates the action of acidic fibroblast growth factor by prolonging its biological half-life", *J. Cell Physiol.*). For instance, the proliferative effect of ECGF on vascular endothelial cells is potentiated by heparin (Thornton, S. C., S. N. Mueller, and E. M. Levine, "Human endothelial cells: use of heparin in cloning and long-term serial cultivation", *Science,* 222:623–625 (1983)).

It is well known that heparin binds ECGF (Maciag, T., T. Mehlman, and R. Friesel, "Heparin binds endothelial cell growth factor, the principal endothelial cell mitogen in bovine brain", *Science,* 225:932–935 (1984)) and potentiates the effect of ECGF, for instance, on the growth of human endothelial cells (S. C. Thornton et al., supra). Several workers have shown that heparin prolongs the biologic half-life of growth factors by protection from proteolytic degradation (B. Lyons-Giordano et al., supra), and acid and heat inactivation (Gospodarowicz, D. and J. Cheng, "Heparin protects basic and acidic fibroblast growth factor from inactivation", *J Cell Physiol* , 475–484 (1986)). In addition, heparin increases the affinity of ECGF for cell surface receptors by inducing conformational changes in the ECGF peptide (Schreiber, A. B., J. Kenney, J. Kowalsky, R. Freisel, T. Mehlman, and T. Maciag, "The interaction of endothelial cell growth factor with heparin: characterization by receptor and antibody recognition", *Proc. Natl. Acad. Sci. USA,* 82:6138–6142, (1985)).

Tan, E. M. L., E. Levine, T. Sorger, G. A. Unger, N. Hacobian, B. Planck, and R. V. Iozzo, "Heparin and endothelial cell growth factor modulate collagen proteoglycan production in human smooth muscle cells", *Biochem. Biophys. Res. Commun.*, 163:84–92 (1989) disclose the effects of heparin and endothelial cell growth factor (ECGF) on extracellular matrix production in human iliac smooth muscle cells. The cells were grown in a medium supplemented with heparin and ECGF, medium supplemented with ECGF and unsupplemented medium. In the presence of heparin and ECGF, collagen production was inhibited 91–95% as compared to cultures incubated with ECGF alone or without both supplemental factors. In contrast, the production of proteoglycans was elevated 2.5 fold in the presence of heparin and ECGF. Enzymatic digestion of the proteoglycans indicated that both large and small molecular weight chondroitin sulfate proteoglycans were markedly elevated, while dermaton sulfate and heparin sulfate proteoglycans were increased to a lesser extent suggesting that a combination of heparin and ECGF elicits modulation of extracellular matrix production in smooth muscle cells, with divergent effects on collagen and proteoglycan synthesis. Furthermore, it was determined that heparin exerts a coordinate down-regulation of various matrix genes, that include the collagen, fibronectin and decorin genes, in smooth muscle cells.

U.S. Pat. No. 4,879,287 (Saliba) discloses a broad spectrum of medical applications for heparin and related molecules. It describes heparin's prevention of cell and tissue destruction and promotion of healing. The use of heparin for keloid prevention is taught. The invention comprises applying heparin/heparin-like compounds, either in solution or in the form of cream or aerosol, preferably at a pH of about 5.5, in an effective amount for a time sufficient to effect treatment. The concentration of heparin/heparin-like compounds is between 1500–5000 I.U./ml.

U.S. Pat. No. 4,745,098 (Michaeli) discloses compositions to improve wound healing comprising a suspension of collagen and glycosaminoglycan, such as heparin. Concentrations of collagen of 7–10 mg/ml in combination with 250–350 μg/ml of the glycosaminoglycan are taught.

U.S. Pat. No. 4,837,024 (Michaeli) relates to compositions of fibrous protein, collagen, and a polysaccharide such as heparin which are applied with a bandage article to promote the healing of wounds.

U.S. Pat. No. 4,808,570 (Michaeli) discloses a suspension comprising fibrous protein, collagen, and glycosaminoglycan such as heparin used to improve the healing of wounds. The application promotes vascularization and attracts fibroblasts and endothelial cells by chemotaxis. The invention is particularly useful in treating persistent ulcerated wounds.

U.S. Pat. No. 4,760,131 (Sundsmo et al.) discloses a topical aqueous composition comprising fibrillar collagen, heparin and ungranulated platelets or platelet releasate which promotes collagen syntheses and wound healing.

In the majority of the prior art modalities for the treatment of skin fibrotic and other cirrhotic diseases, however, variable success has been encountered. Therefore, alternative efficacious therapies are still needed. An effective method of modulating collagen synthesis would therefore be useful therapeutically.

SUMMARY OF THE INVENTION

We have found that collagen biosynthesis, as measured by hydroxyproline synthesis, was markedly inhibited by the composition of the instant invention comprising an endothelial cell growth factor (ECGF) either alone or in combination with and heparin or a heparin-like compound. Useful endothelial cell growth factors include ECGF, acidic fibroblast growth factor (aFGF) and basic fibroblast growth factor (bFGF). Fibroblast cultures incubated with ECGF alone demonstrated a measurable decrease in collagen synthesis, as compared to control cultures. For example, at a concentration of 75 μg/ml ECGF, collagen synthesis was decreased approximately 50%. A concentration of at least 25 μg/ml ECGF is effective. In the presence of 75 μg/ml of ECGF and concentrations of heparin from 100 μg/ml to 500 μg/ml, the inhibition of total collagen synthesis ranged from 65% to 80% as compared to control cultures that were not supplemented with ECGF or heparin. Quantitative measurements of mRNA-cDNA hybrids revealed that the gene expression of collagen type I was decreased more than 80% by the composition of the present invention. We have found that ECGF and heparin elicit a negative regulatory effect on collagen production. Thus, a novel modality of treatment employing an endothelial cell growth factor either alone or in a combination with and heparin or a heparin-like compound for localized dermal fibrotic conditions, such as keloids, hypertrophic scars and linear and generalized morphea, is provided.

DETAILED DESCRIPTION OF THE DRAWINGS

FIGS. 1 (1a)–(1b) are a graphical depiction of the effects , of ECGF and heparin on [$^3$H]hydroxyproline synthesis by keloid skin fibroblasts.

FIGS. 2 (1a)–(1b) are a graphical depiction of the effects of ECGF and heparin on [$^3$H]hydroxyproline synthesis associated with cell layer.

FIGS. 3 (1a)–(1b) are a graphical depiction of the effects of ECGF and heparin on collagen production released in medium of keloid fibroblasts.

FIGS. 5 A–H are photographs depicting the results of indirect immunofluorescence staining for type I collagen.

FIGS. 6 A and B are a graphical (A) and photographic (B) depiction showing the inhibition of collagen gene expression by ECGF and heparin.

DETAILED DESCRIPTION OF THE INVENTION

A consistent and dramatic inhibition of collagen synthesis was observed by biochemical and immunostaining methods in all strains of keloid fibroblasts that were incubated with an endothelial cell growth factor either alone or in combination with heparin. ECGF, is known to be mitogenic for a variety of cell types and was found to increase the DNA and cell protein contents of keloid fibroblasts. ECGF was found to be a potent inhibitor of collagen biosynthesis in keloid skin fibroblasts. The inhibitory effect is largely explained by the action of ECGF on the mRNA level.

Heparin alone did not reduce collagen production as much as ECGF. However, when heparin was combined with ECGF, collagen synthesis and the gene expression of type I collagen were both greatly decreased to a greater extent than by ECGF alone, thereby, suggesting that heparin potentiates the action of ECGF when it binds the growth factor. At high concentrations, particularly at 500 μg/ml, heparin was found to increase the mRNA level for pro-alpha 1(I) of type I collagen. The high abundance of the mRNAs is apparently reflected in the elevated amount of newly-synthesized hydroxyproline in the cell layer when the cells are incubated with heparin. Heparin may also influence the translational and post-translational activities resulting in increased cellular hydroxyproline synthesis. Immunostaining with the antibody to type I collagen also revealed the intracellular accumulation of collagen by heparin. However, the biochemical data show that, at the same concentrations of heparin, decreased amounts of hydroxyproline are secreted into the medium compartment, and that the overall amount of newly-synthesized collagen is reduced. The reason for the apparent decrease in the secretion of collagen is not known; it is possible that the intracellular collagen is abnormal or that the collagen binds to the internalized heparin and its fragments, and is not secreted at the normal rate.

The instant invention, comprising an endothelial cell growth factor such as ECGF, aFGF or bFGF, or in its preferred embodiment, a combination of ECGF and heparin or a heparin-like compound, is a potent inhibitor of collagen synthesis. The reduced production of collagen can be explained largely to a selective down-regulation of the pro-alpha 1(I) of type I collagen gene expression, resulting in diminished levels of the corresponding mRNA transcripts. Thus, the invention affords a new therapeutic approach to the treatment of keloids and other localized cutaneous dermal fibrotic diseases.

In the preferred embodiment, heparin and ECGF, aFGF or bFGF either alone or in combination with a pharmaceutically acceptable carrier are administered by intralesional injection into the keloid or scar tissue. Alternatively, a form of topical application, (i.e., cream or ointment) affords some efficacy, but would be more beneficial if administered post-surgically over the wound following excision of the keloid to prevent recurrence of the keloid at that site. The preferred concentration ranges of the growth factor and heparin will depend on whether the administration is by injection or topical. It is well known in the art that an injection requires a lower effective concentration than a topical application. For example, the preferred concentration of a growth factor, such as ECGF, is at least 25 µg/ml when applied topically. An effective concentration range for topical application is about 25 µg/ml to about 250 µg/ml and about 100 µg/ml to about 1000 µg/ml of heparin. For injection, a concentration of at least 2.5 µg.ml of a growth factor such as ECGF is efficacious. A concentration range for administration by injection is at about 2.5 µg/ml to about 100 µg/ml with about 10 µg/ml to about 500 µg/ml heparin in a preferred embodiment.

Further, application of heparin and ECGF, or aFGF or bFGF, may be extended to treatment of solar-induced aging skin based upon our finding that heparin and ECGF stimulate the production of proteoglycans, an extracellular matrix component that functions in the hydration properties of tissues. It is generally thought that deficient hydration is one of the causative factors of aging tissue. Therefore, restoration of hydration to aging skin may be a benefit derived from the employment of heparin and ECGF, aFGF or bFGF, either alone or in combination with a pharmaceutically acceptable carrier.

The invention is further illustrated by means of the following examples. These examples are meant to be illustrations only and are not intended to limit the present invention to the specific embodiments.

EXAMPLES

Example 1

Cell culture. Human skin fibroblast cultures were established from excised keloid tissue from six patients, 20 to 30 years of age. These patients did not present with any known systemic conditions. Tissue samples were cut into small pieces and explanted in tissue culture flasks. Within one to two weeks, fibroblasts grew from the explants and were subcultured in Dulbecco's modified Eagle's medium (GIBCO, Grand Island, New York, N.Y.) supplemented with 10% fetal bovine serum, 200 U/ml of penicillin, 200 µg/ml of streptomycin (GIBCO, Grand Island, New York, N.Y.). Confluent cultures were trypsinized and subcultured in 75 cm² flasks (Falcon Plastics). Cells in passages 6 to 10 were employed for the experiments described below.

Example 2

Indirect Immunofluorescence. The fibroblasts were cultured on chamber slides (Lab Tek, Nunc Inc., Naperville, Ill.) and grown to early confluency. The cells were incubated for four days (a) without ECGF or heparin (control), (b) 75 µg/ml of ECGF derived from bovine neural tissue (Sigma Chemical Co., St. Louis, Mo.), (c) 500 µg/ml of heparin from porcine intestinal mucosa (Grade I, Sigma Chemical Co., St. Louis, Mo.), and (d) ECGF (75 µg/ml) combined with heparin (500 µg/ml). The media were changed on the third day, the cells were then fixed on the fourth day in cold (−20° C.) ethanol and pre-incubated for 15 minutes with Tris-buffered saline (TBS) containing 1% bovine serum albumin (BSA) to block nonspecific antibody binding. The samples were exposed to rabbit antibody against human type I collagen (IgG, Pasteur Institute, Lyon, France) in appropriate dilutions in TBS-BSA overnight at 4° C. The samples were washed in TBS for 60 minutes with five changes, and incubated with tetramethyl-rhodamine isothiocyanate (TRITC)-conjugated secondary antibodies (Miles Laboratories, Inc., Elkhard, Ind.). After a 60 minute incubation at room temperature, the samples were washed with TBS for 60 minutes, rinsed with distilled water, mounted and examined with a fluorescence microscope (Nikon Optiphot), equipped with filters for detection of TRITC. In control reactions, the primary antibody was omitted or replaced with sera from non-immunized animals. Negligble background was observed in the control samples.

Example 3

Assay for procollagen production. Human skin fibroblasts were grown to confluency in 25 cm² flasks. The cells were incubated (a) without heparin or ECGF (control), (b) with 75 µg/ml of ECGF, (c) with 100, 250, and 500 µg/ml of heparin, and (d) combinations of 75 µg/ml of ECGF with 100, 250, or 500 µg/ml of heparin in triplicate flasks for each of the culture conditions for a total of four days. The media were changed on the third day and replaced with that containing the identical respective supplements. Ascorbic acid, 35 µg/ml, was added to each flask and preincubation was performed for two hours prior to the addition of 20 µCi of L-[2,3,4,5-$^3$H]proline (108.6 Ci/mmol., New England Nuclear, Boston, Mass.). The cells were incubated for an additional 18 hours with the radioisotope at 37° C. The incubation was terminated by removing the medium, cooling the medium at 4° C., and adding the following protease inhibitors to give final concentrations of 20 mM $Na_2EDTA$, 10 mM NEM and 1 mM PMSF. The cell layer was rinsed twice with 0.5 ml of PBS and scraped into 2 ml of solution containing 0.4 M NaCl, 50 mM Tris-HCl (pH 7.4), and the same protease inhibitors. The cells were sonicated at 50 Hz for 30 sec. To quantitate the synthesis of $[3_H]$hydroxyproline, an index of procollagen synthesis, aliquots of medium and cell fractions were dialyzed against several changes of deionized water, hydrolyzed in 6N HCl at 115° C. for 24 hours, and assayed for nondialyzable $[3_H]$hydroxyproline, employing a specific radiochemical method, i.e., Juva, J. and D. J. Prockop, "Modified procedure for the assay of $H^3$- or $C^{14}$-labeled hydroxyproline", *Anal. Biochem.* 15:77–83 (1966). The synthesis of $[3_H]$hydroxyproline was normalized for cellular protein (Bradford, M. M., "A rapid and sensitive method for the quantitation of microgram quantities of protein utilizing the principle of protein-dye binding" Anal. *Biochem.*, 72:248–254 (1976)) and DNA contents (Burton, K., "Determination of DNA concentration with diphenylamine", *Methods Enzymol.* 12B:163–166 (1968)). Confluent triplicate flasks were analyzed in parallel for each of the experimental conditions.

Example 4

Quantitation of mRNA levels by Slot Blot analysis. Keloid fibroblasts were grown to confluency in 75 cm² flasks and were then incubated in the following conditions: (a) without heparin or ECGF (control), (b) 75 µg/ml of ECGF, (c) 100, 250 and 500 µg/ml of heparin, and (d) the combinations of 75 µg/ml of ECGF with 100, 250, or 500 µg/ml of heparin. Total RNA was isolated from confluent cell cultures by extracting the cells with 4 M guanidinium isothiocyanate, pH 7.0, containing 5 mM sodium citrate, 0.5% (w/v) sarkosyl, 0.1 M 2-mercaptoethanol, and 0.1% Antifoam A emulsion. The samples were subjected to cesium chloride density gradient ultracentrifugation at 150, 0000× g for 18 hours at 15° C. and the RNA was precipitated by ice-cold ethanol as described before (Oikarinen, H., A.I. Oikarinen, E. M. L. Tan, R. P. Abergel, C. A. Meeker, M. L. Chu, D. J Prockop, and J. Uitto, "Modulation of procollagen gene expression by retinoids", *J clin Invest*, 75:1545–1553 (1985)). The amount of RNA was quantitated by spectrophotometric absorbance at 260/280 nm. Quantitation of the mRNA transcripts was performed by slot blot analysis. Serially diluted concentrations of total RNA from fibroblasts incubated in the various culture conditions were applied to nitrocellulose membranes, employing a vacuum manifold apparatus (Minifold II, Schleicher and Schuell, Keene, N.H.). The RNAs were immobilized by heat at 78° C. for 90 minutes under vacuum. (Oikarinen et al., supra.) Prehybridization and hybridization with the human cDNA probes described below were performed by labeling with [$32_P$] dCTP by nick translation (Maniatis, T., A. Jeffrey, and D. G Kleid, "Nucleotide sequence of the rightward operator of phage" *Proc. Natl. Acad. Sci. USA*, 72:1184–1188 (1975)), to a specific activity of approximately $10^8$ to $10^9$ cpm/ μg DNA. The prehybridization and hybridization solutions contained 3× SSC (1× SSC =0.15 M NaCl, 15 mM sodium citrate), pH 6.8, 50% formamide, 0.1% sodium dodecyl sulfate (SDS), 250 μg/ml denatured salmon sperm DNA, and 1 × Denhardts solution (0.1% polyvinylpyrolidone, 0.1% bovine serum albumin and 0.1% Ficoll). The hybridization was performed at 42° C. for 12–24 hours (Uitto, J., A. J. Perejda, R. P. Abergel, M. L. Chu, and F. Ramirez, "Altered steady-state ratio of type I/type III procollagen mRNAs correlates with selectively increased type I procollagen biosynthesis in cultured keloid fibroblasts", *Proc. Natl. Acad. Sci. USA*, 82:5935–5939 (1985)). The membranes were washed several times at 65° C. with a final stringency wash of 0.1× SSC containing 0.1% SDS.

Example 5

Northern Transfer analysis. To establish the specificity of the hybridizations with the human cDNA probes, Northern transfer analysis was conducted. Total RNA samples were electrophoresed in 1% agarose gels under denaturing conditions and processed for Northern blotting as described previously (Thomas, P.S., Hybridization of denatured RNA and small DNA fragments transferred to nitrocellulose", *Proc Natl Acad Sci USA*, 77:5201–5205 (1980)). The prehybridization and hybridization conditions were similar as those for the slot blot analysis.

The nitrocellulose filters from Northern transfer and slot blot analysis were exposed to XOMAT-AR films (Kodak, Rochester, N.Y.) between intensifying screens (Kodak, Rochester, N.Y.). The autoradiograms were scanned with a He—Ne laser densitometer (LKB, Bromma, Sweden) the absorbance units were corrected for the specific activities of the probes and expressed as units/ μg RNA.

cDNA probes. The human cDNA probes employed in the slot blot and Northern transfer analyses included: a 1.5 kb pro-alpha 1(I) (HF-677) cDNA corresponding to the COOH-terminal propeptide and the carboxy-terminal portion of the triple helical region of human pro-alpha 1(I) chain of type I procollagen (Chu, M. L., J. C. Myers, M. P. Bernard, D. F Ding, and F Ramirez, "Cloning and characterization of five overlapping cDNAs specific for the human pro-alpha 1(I) collagen"*Nucleic Acids Res.*, 10:5925–5934 (1982)); a 1.7 kb fibronectin (HF-771) cDNA corresponding to the COOH-terminal portion of human cellular fibronectin (Bernard, M. P., M. Kolbe, D. Weil, and M. L. Chu, "Human cellular fibronectin: comparison of the carboxyl-terminal portion with rat identified primary structural domain separated by hypervariable regions"*Biochemistry*, 24:2698–2704 (1985)); a 1.7 kb beta-actin (pHF A-I) cDNA (Ponte, P., P Gunning, H. Blau, and L Kedes, "Human actin genes are single copy for alpha-skeletal and alpha-cardiac actin but multicopy for beta- and gamma-cytoskeletal genes: 3' untranslated regions are isotype specific but are conserved in evolution", *Mol cell Biol.*, 3:1783–1791 (1983)).

Example 6

Figure 1A:
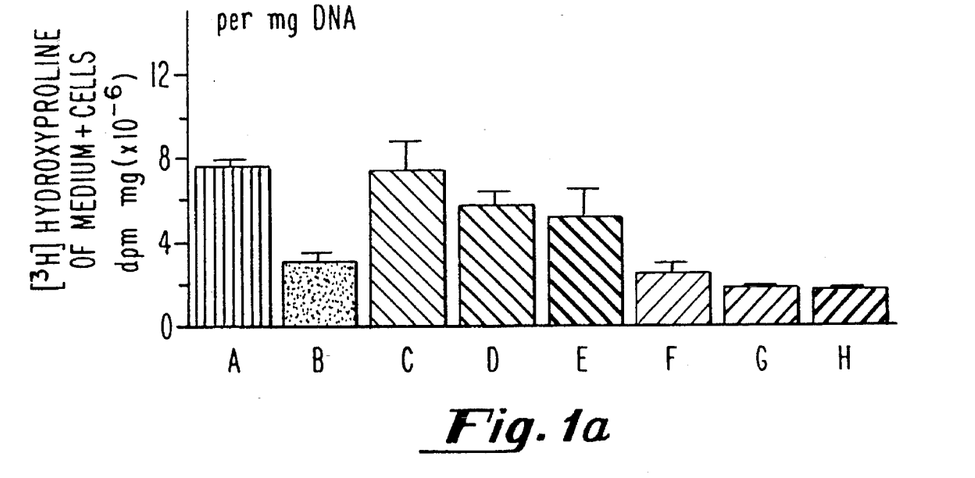
Figure 1B:
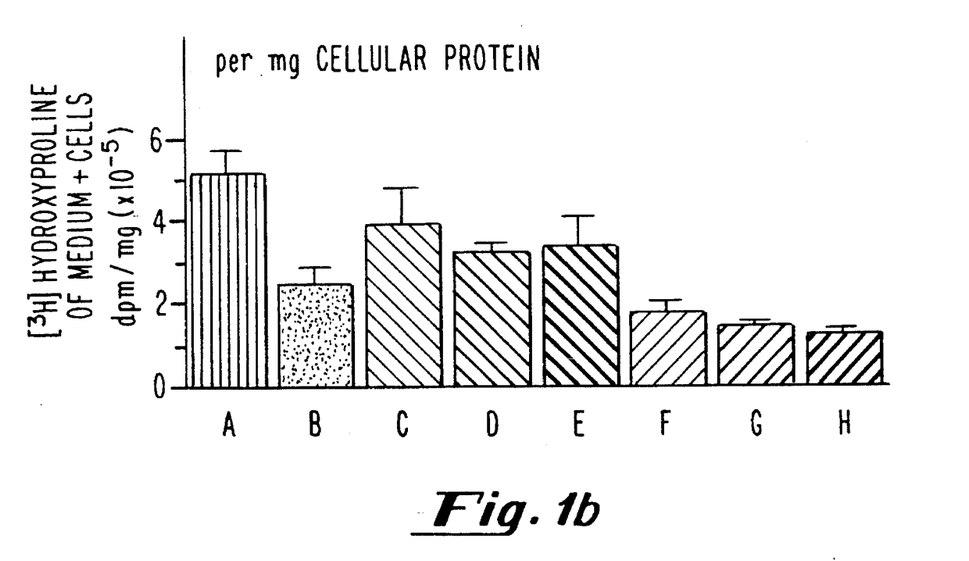

Effects of ECGF and heparin on [$3_H$]hydroxyproline synthesis. Newly-synthesized collagen synthesis, as measured by the amount of [$3_H$]hydroxyproline synthesized and normalized by the amount of DNA or cellular protein content, was dramatically inhibited by ECGF alone (Bar B FIG. 1a–1b) and by the combination of ECGF and heparin Bar F-H (FIG. 1a–1b). ECGF (Bar B FIG. 1a–1b) caused a 51% to 59% decrease in total [$3_H$]hydroxyproline synthesis as compared to control cultures (Bar A, FIG. 1a–1b). The inhibitory effect by heparin (100, 250, and 500 μg/ml) was small (Bar C-E, FIG. 1a–1b); the percent inhibition of 250 μg/ml and 500 μg/ml of heparin (Bar D,E, respectively, FIG. 1a–1b) was approximately 25% to 36% relative to control cultures (Bar A, FIG. 1a–1b). However, in cell cultures incubated with the combination of heparin and ECGF, the suppression of [$3_H$]hydroxyproline synthesis was dramatic (Bar F-H, FIG. 1a–1b). Indeed, the combination of heparin (100, 250, and 500 μg/ml) and ECGF (75 μg/ml) caused a 65% to 77% inhibition of collagen production relative to non-treated control cultures (Bar F-H, FIG. 1a–1b respectively). The inhibition was more pronounced than that by ECGF alone. At the highest concentration of heparin, 500 μg/ml, combined with ECGF (Bar H, FIG. 1a–1b), collagen production was 50% of that in cultures incubated with ECGF alone (Bar A, FIG. 1a–1b). The latter data show that heparin exerts an additive inhibitory effect when combined with ECGF.

Figure 2A:
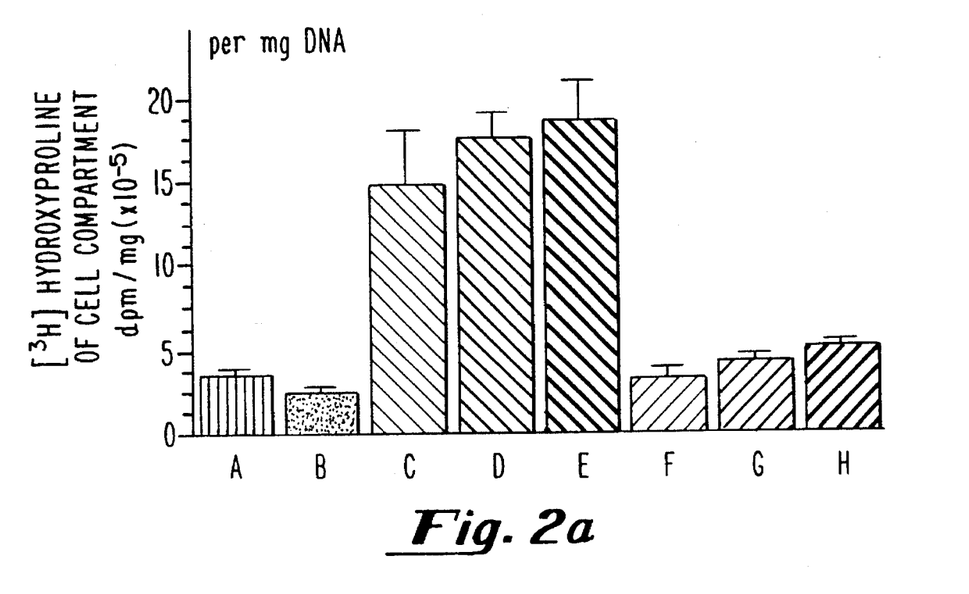
Figure 2B:
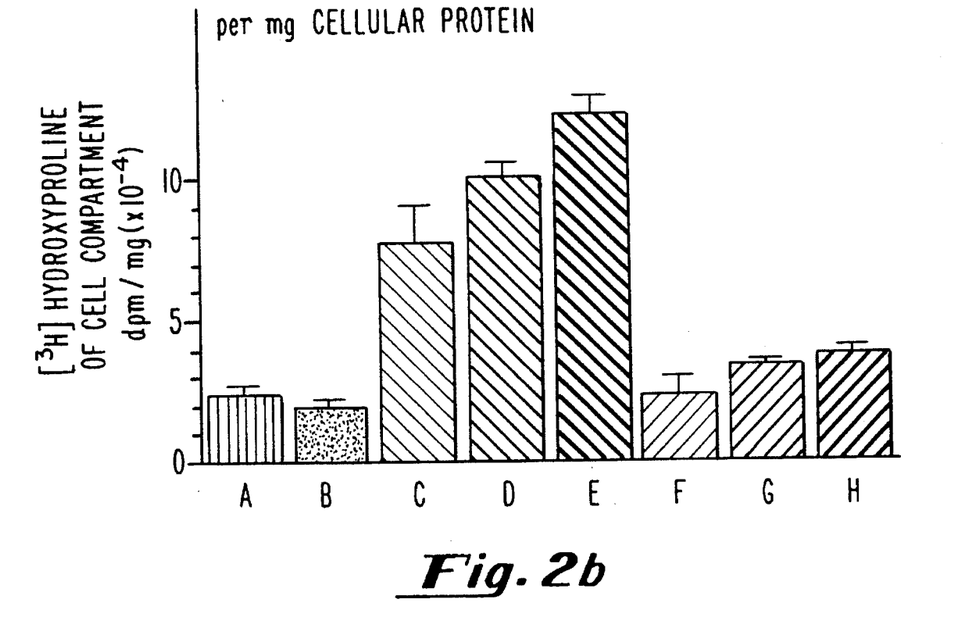

Heparin caused an increased accumulation of [$3_H$]hydroxyproline associated with the cell layer (Bar C-E FIG. 2a–2b), relative to that of the control (Bar A, FIG. 2a–2b) and ECGF-treated cells (Bar B, FIG. 2a–2b). The accumulation was dependent upon the concentration of heparin. ECGF alone did not promote the accumulation in the cell layer (Bar B, FIG. 2a2b). However, in cultures incubated with ECGF combined with increasing concentrations of 100, 250, and 500 μg/ml of heparin (Bar F-H, FIG. 2a–2b, respectively), a similar trend of enhanced accumulation of [$3_H$]hydroxyproline, albeit much less than that observed with heparin alone (Bar C-E, FIG. 2a–2b), was found in the cell layer.

Figure 3A:
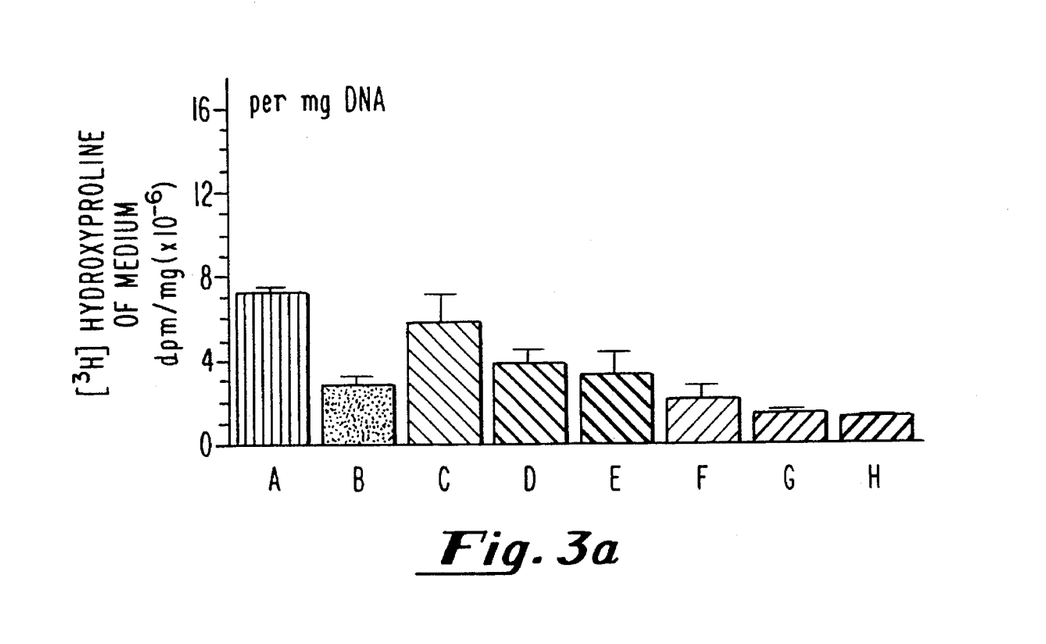
Figure 3B:
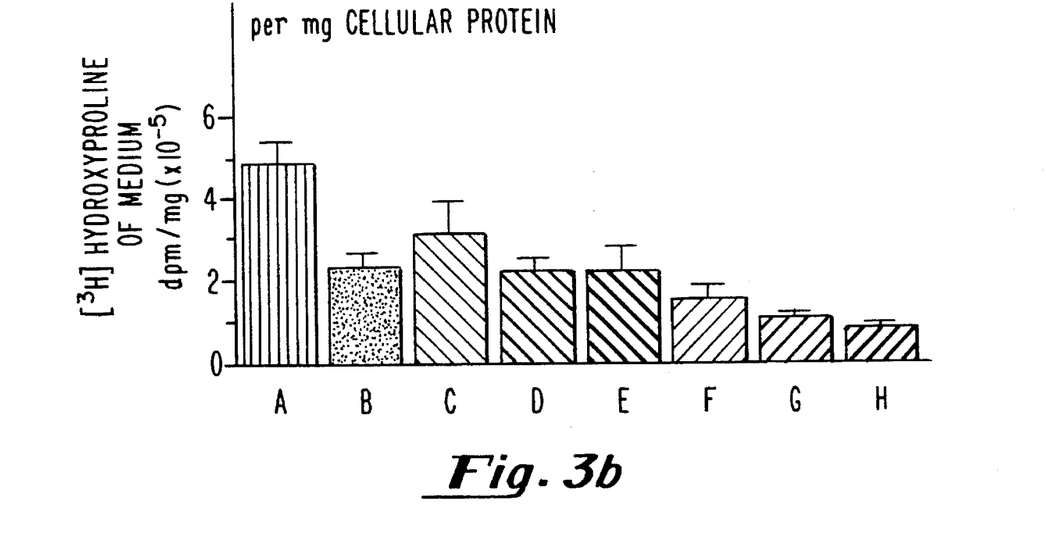

In the medium compartment, ECGF (FIG. 3B) decreased the amount of (3H]hydroxyproline synthesis by approximately 50% or more compared to parallel control cultures (Bar A, FIG. 3a–3b). Decreased quantities of newly-synthesized $3_H$-collagen were also found in the media of cultures incubated with heparin alone (100, 250, and 500 μg/ml) (Bar C-E, FIG. 3a–3b, respectively) and in combination with ECGF (Bar F-H, FIG. 3a–3b). The reduction of 3H-procollagen in the medium was related to suppressed collagen synthesis as well as to the decreased secretion of collagen by heparin (FIG. 4).

Figure 4:
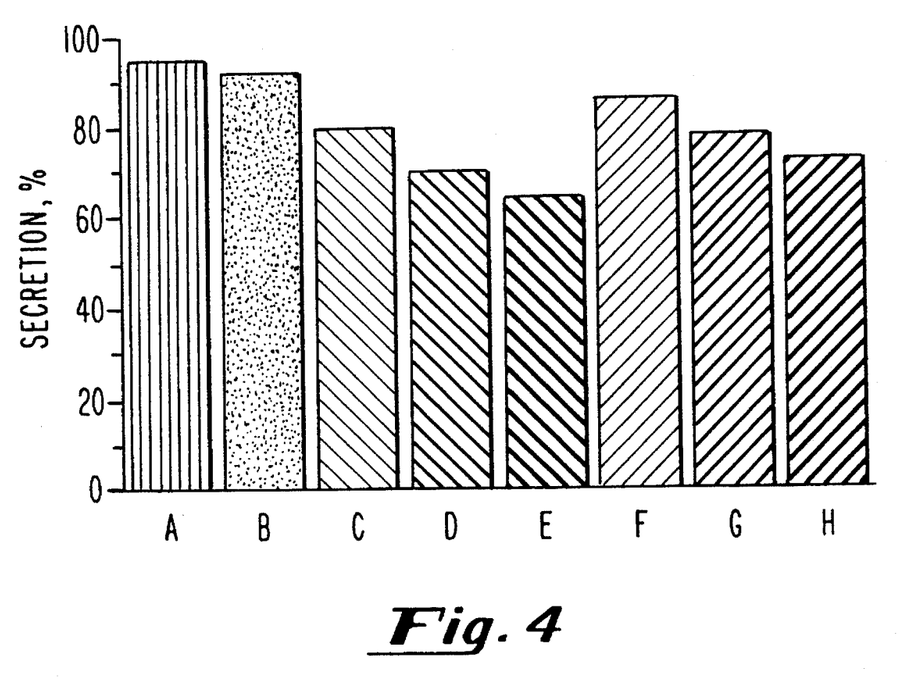
FIG. 4 is a graphical depiction of the effect of heparin on the amount of collagen secreted.
Figure 5A:
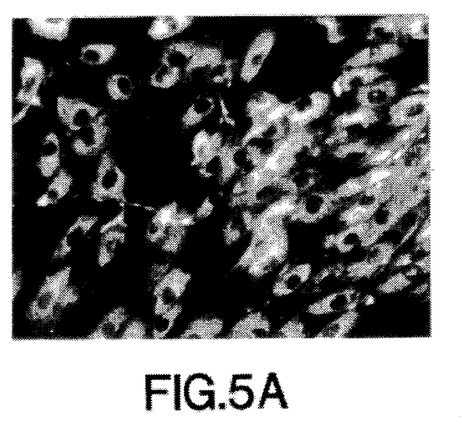
Figure 5B:
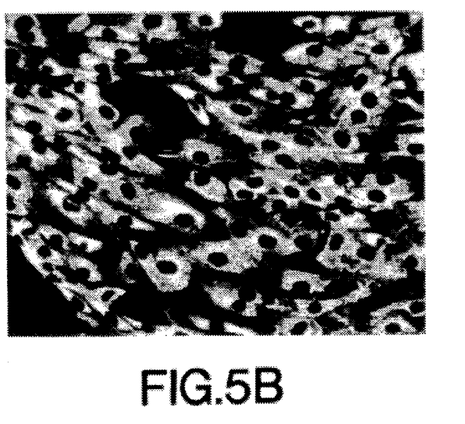
Figure 5C:
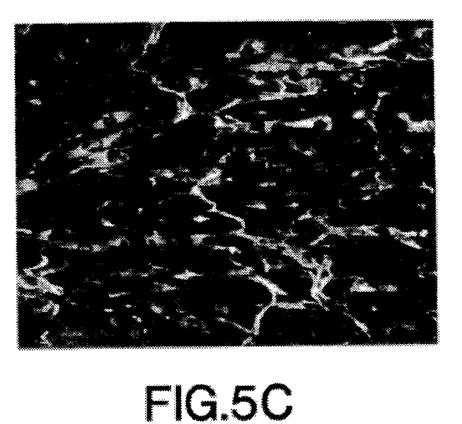
Figure 5D:
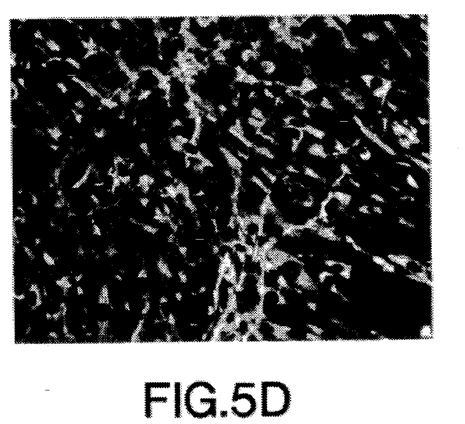
Figure 5E:
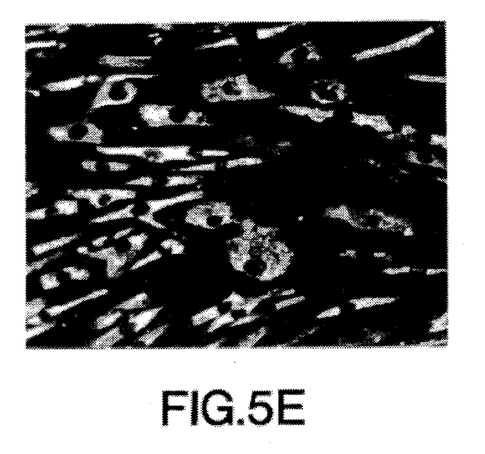
Figure 5F:
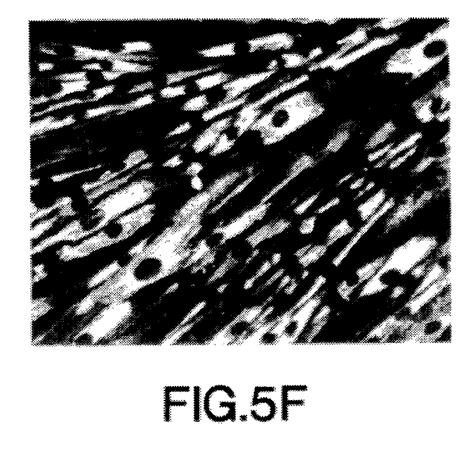
Figure 5G:
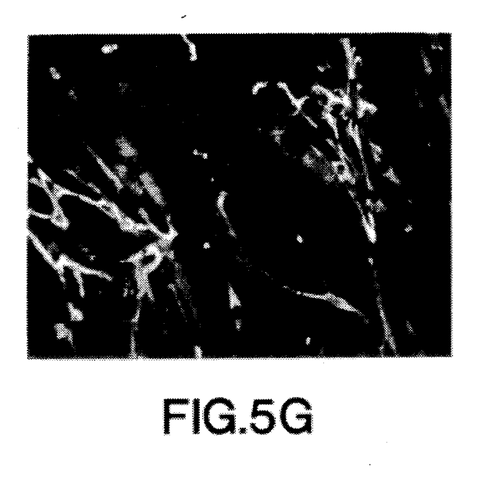
Figure 5H:
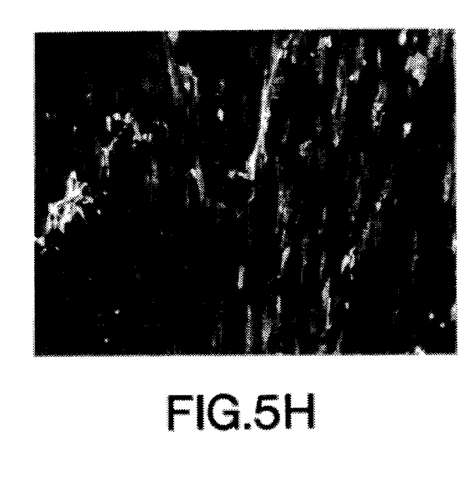

ECGF did not affect the secretion of collagen (Bar A, FIG. 4). Heparin, at 100, 250, and 500 μg/ml (Bar C-E, FIG. 4, respectively) inhibited collagen secretion in a dose-response manner. A similar, but less inhibitory, effect on collagen secretion was noted when the cells were incubated with the combination of the three concentrations of heparin and ECGF (Bar F-H, FIG. 4, respectively).

Other analyses. Cellular protein and DNA analyses revealed that while heparin had no effect, ECGF (75 µg/ml) had a stimulatory effect on protein and DNA contents, suggesting the ECGF exerts a mitogenic effect on skin fibroblasts (Table 1).

Example 8

Inhibition of collagen gene expression by ECGF and heparin. Slot blot analysis using the human cDNA probe for pro-alpha 1(I) of type I procollagen demonstrated a marked decrease in the mRNA level for type I procollagen in keloid fibroblast cultures that had been incubated with 75 µg/ml of ECGF (FIG. 6a–6b)- The mRNA level was decreased 75% by ECGF (Bar B, FIG. 6a–6b) as compared to the control cultures (Bar A, FIG. 6a–6b). In cultures incubated with ECGF and heparin (100 and 500 µg/ml), the expression of

TABLE 1

| Cells | Control | ECGF 75 µg/ml | 100 µg/ml | 250 µg/ml | 500 µg/ml |
|---|---|---|---|---|---|
| | | | ECGF (75 µg/ml) + Heparin | | |
| DNA (µg) | 9.3 ± 0.7 | 14.7 ± 0.8 | 15.4 ± 1.0 | 14.4 ± 0.7 | 15.3 ± 0.5 |
| Protein (mg) | 0.14 ± 0.01 | 0.18 ± 0.01 | 0.21 ± 0.01 | 0.18 ± 0.01 | 0.21 ± 0.01 |
| | | | Heparin | | |
| DNA (µg) | 9.3 ± 0.7 | 14.7 ± 0.8 | 8.6 ± 0.5 | 9.9 ± 0.2 | 9.9 ± 1.0 |
| Protein (mg) | 0.14 ± 0.01 | 0.18 ± 0.01 | 0.16 ± 0.00 | 0.15 ± 0.01 | 0.21 ± 0.01 |

[1]Confluent keloid fibroblasts were incubated for four days in triplicate flasks under each of the above growth conditions. The cell layer was extracted and analyzed for DNA and protein contents as detailed in the methods.
[2]The values represent the means ± S.D. of triplicate flasks, each of which was analyzed in duplicate samples.

Example 7

Figure 6A:
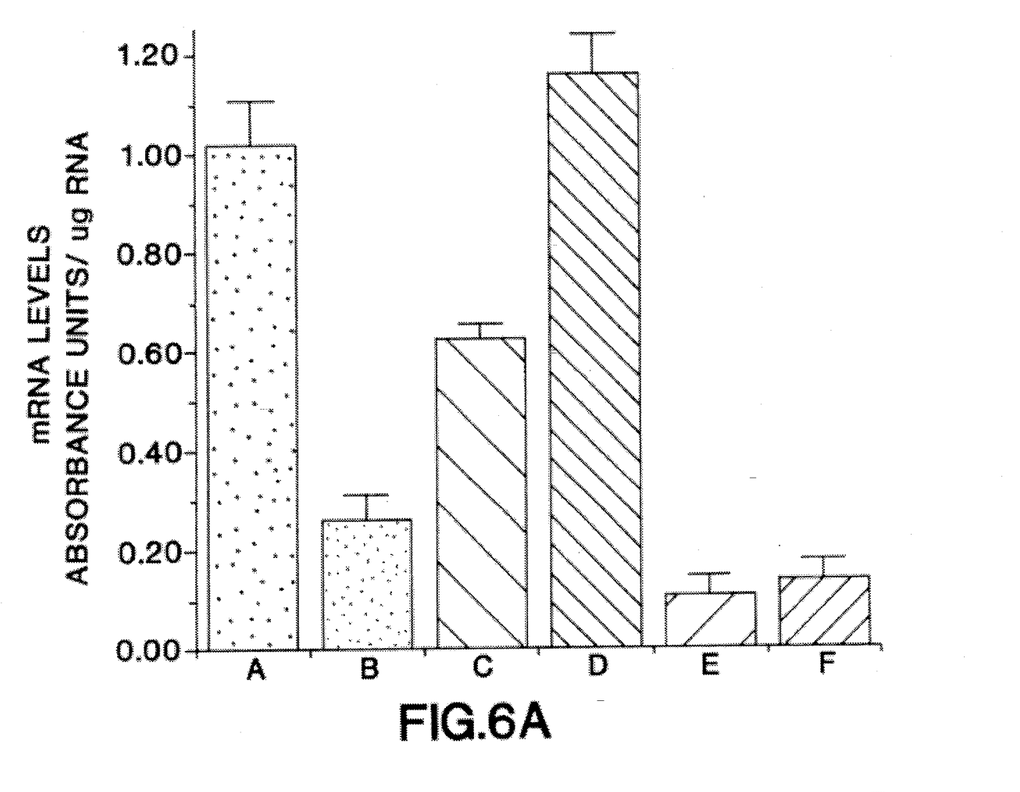
Figure 6B:
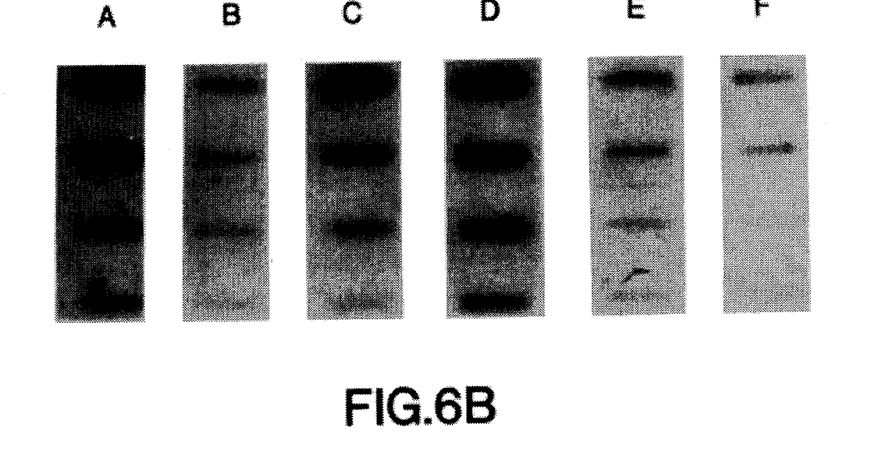

Immunofluorescence microscopy of keloid skin fibroblasts incubated with ECGF and heparin. Previously, we noted that increased [3$_H$]hydroxyproline was associated with the cell layer in the presence of heparin. Immunofluorescence microscopy, using antibodies that recognized the type I collagen epitopes, revealed that there were major differences in the distribution of the type I collagen in the cell cultures maintained in ECGF and heparin as well as those without the supplemental factors. Type I collagen was detectable in normal (Bar A-D, FIG. 5) and keloid skin fibroblasts (Bar E-H, FIG. 5). In the cultures that were maintained in the presence of heparin, type I collagen was mostly intracellular (Bar B and F, FIG. 5). The immunofluorescence intensity was considerably increased in the heparin-treated cells (Bar Band F, FIG. 5) as compared to the ECGF-treated cultures (Bar Card G, FIG. 5) and those incubated with both heparin and ECGF (Bar D and H, FIG. 5). The cells that were incubated with 75 µg/ml of ECGF (Bar C and G, FIG. 5) demonstrated a reduced level of immunofluorescence, indicating a decreased amount of intracellular type I collagen. Incubation with ECGF resulted in the deposition of the type I collagen into a fine extracellular network. In cultures that were incubated with both ECGF and heparin (Bar D and H, FIG. 5), there was some intracellular accumulation of the collagen, but much less than that with heparin treatment alone (Bar B and F, FIG. 5). In addition, a network of fibers was deposited extracellularly (Bar C, D, G, H, FIG. 5). Thus, the presence of type I collagen as seen in immunofluorescence microscopy in normal and keloid fibroblasts is distributed differently by ECGF and heparin. ECGF (Bar C and G, FIG. 5) decreased the intracellular accumulation of type I collagen as compared to the untreated (Bar A and E, FIG 5) and heparin-treated cultures (Bar and F, FIG 5).

the collagen type I gene was inhibited by 80% to 90% (Bar E and F, FIG. 6a–6b). Heparin alone, at concentrations of 100 and 500 µg/ml, did not cause a major inhibition of collagen gene expression (Bar C and D, FIG. 6a–6b).

Heparin at a concentration of 100 µg/ml (Bar C, FIG. 6a–6b) caused a decrease of 37% in the mRNA level as compared to the control cultures (Bar A, FIG. 6a–6b). However, with 500 µg/ml of heparin, there was increased expression of the mRNA encoding procollagen type I (Bar D, FIG. 6a–6a). Thus, at the mRNA level, ECGF has a potent inhibitory effect on the expression of the pro-alpha 1(I) of type I procollagen gene.

Figure 7:
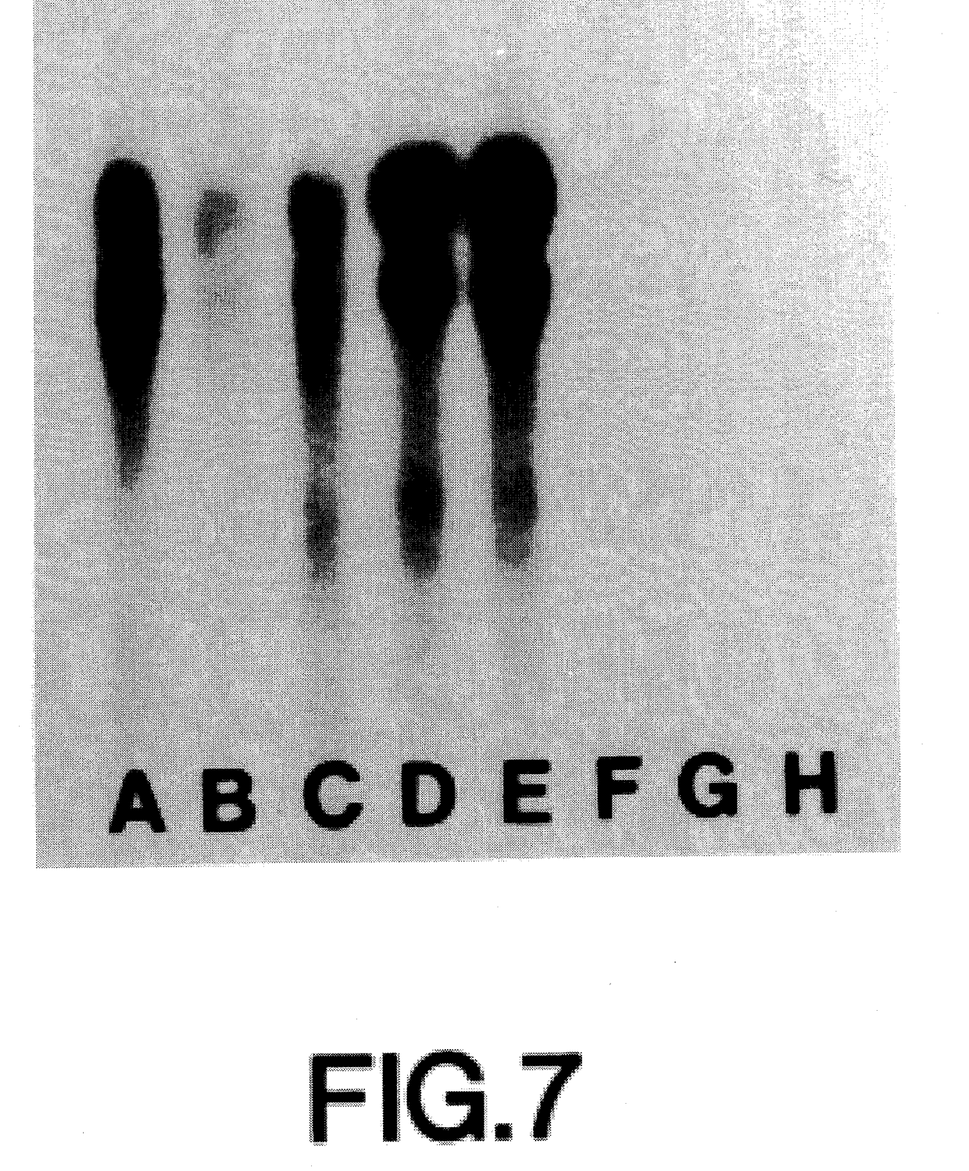
FIG. 7 is a photograph showing the effects of ECGF and heparin on keloid fibroblast expression of pro-alpha 1(I) of type I procollagen mRNA analyzed by Northern transfer analysis.

Northern transfer analysis confirmed the specificity of the hybridization of mRNAs with the pro-alpha 1(I) collagen type I cDNA. The mRNA transcripts consisted of two bands of 5.8 and 4.8 kb, characteristic for pro-alpha 1(I) of type I collagen. ECGF, at 75 µg/ml, caused a dramatic decrease in the mRNA level of pro-alpha 1(I) of type I collagen (Bar B, FIG. 7), relative to the non-treated control samples (Bar A, FIG. 7). Heparin, at 100 µg/ml (Bar C, FIG. 7), suppressed collagen gene expression to a much lesser extent than ECGF (Bar B, FIG. 7). However, at 250 µg/ml and 500 µg/ml (Bar D and E, respectively FIG. 7), heparin had the opposite effect in inducing a greater abundance of mRNAs for type I collagen. This effect appears to be concentration-dependent. When ECGF at 75 µg/ml was combined with 100, 250, and 500 µg/ml of heparin, the expression of the pro-alpha 1(I) of type I collagen gene was inhibited (Bar F, G, and H, FIG. 7); the amount of the mRNAs was decreased to a level much less than that of ECGF alone (Bar B, FIG. 7). These findings support the data from the slot blot analysis. ECGF down-regulates the gene expression of the type I collagen gene and the effect is potentiated when ECGF is combined with heparin.

What is claimed:

1. A method for inhibiting collagen synthesis by keloid skin fibroblasts comprising providing to said keloid skin fibroblasts an amount of a composition effective to inhibit said collagen synthesis, said composition consisting essentially of endothelial cell growth factor.

2. The method of claim 1 further comprising providing to said keloid skin fibroblasts an amount of heparin effective to increase the inhibitory effect of said endothelial cell growth factor.

3. The method of claim 2 wherein said endothelial cell growth factor and said heparin are provided to said keloid skin fibroblasts by intralesional injection.

4. The method of claim 3 wherein said endothelial growth cell factor is provided in an amount of from about 2.5 μg/ml to about 100 μg/ml and said heparin is provided in an amount of from about 10 μg/ml to about 500 μg/ml.

5. The method of claim 2 wherein said endothelial cell growth factor and said heparin are provided to said keloid skin fibroblasts by topical application.

6. The method of claim 5 wherein said endothelial cell growth factor is provided in an amount of from about 25 μg/ml to about 250 μg/ml and said heparin is provided in an amount of from about 100 μg/ml to about 1000 μg/ml.

* * * * *